United States Patent [19]

Golborn et al.

[11] 3,976,620

[45] Aug. 24, 1976

[54] PHOSPHORUS CONTAINING AMIDES FLAME RETARDANTS

[75] Inventors: Peter Golborn, Lewiston; James J. Duffy, Buffalo, both of N.Y.

[73] Assignee: Hooker Chemicals & Plastics Corporation, Niagara Falls, N.Y.

[22] Filed: June 9, 1975

[21] Appl. No.: 585,270

Related U.S. Application Data

[62] Division of Ser. No. 374,826, June 29, 1974, Pat. No. 3,901,650, which is a division of Ser. No. 239,793, March 30, 1972, Pat. No. 3,823,206.

[52] U.S. Cl. .......... 260/45.9 NC

[51] Int. Cl.² .......... C08J 3/20

[58] Field of Search .......... 260/45.9 NC

[56] References Cited

UNITED STATES PATENTS 3,579,532 5/1971 Nadbur et al. .......... 260/932 X

*Primary Examiner*—V.P. Hoke

*Attorney, Agent, or Firm*—Peter F. Casella; William J. Crossetta, Jr.

[57] ABSTRACT

New compounds are disclosed of the formula:

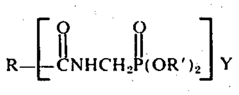

wherein R′ is selected from the group consisting of phenyl, lower alkenyl and halogen substituted and unsubstituted lower alkyl of 1–6 carbon atoms, y is an integer from 1–2 provided that when y is 1, R is selected from the group consisting of hydrogen, lower alkyl of 2–8 carbon atoms, benzyl, dialkylphosphonoalkyl and phenoxymethylene and when y is 2, R is lower alkylene of 1–4 carbon atoms. The compounds of the invention are useful as flame retardant agents for textile materials and in the production of polymers and copolymers which possess flame retardant properties.

16 Claims, No Drawings

PHOSPHORUS CONTAINING AMIDES FLAME RETARDANTS

This is a division, of application Ser. No. 374,826, filed June 29, 1974, now U.S. Pat. No. 3,901,650, issued Aug. 26, 1975 which in turn is a divisional of Ser. No. 239,793, filed Mar. 30, 1972 now U.S. Pat. No. 3,823,206, issued July 9, 1974.

FIELD OF INVENTION

This invention relates to novel compounds of the formula

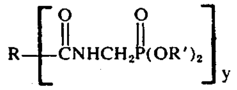

wherein R' is selected from the group consisting of phenyl, lower alkanyl and halogen substituted and unsubstituted lower alkyl of 1–6 carbon atoms, y is an integer from 1–2 provided that when y is 1; R is selected from the group consisting of hydrogen, lower alkyl of 2–8 carbon atoms, benzyl, dialkylphosphonoalkyl and phenoxymethylene and when y is 2, R is lower alkylene of 1–4 carbon atoms. The invention includes methods of applying the above novel compounds to normally flammable textiles and thermoplastic, thermosetting and elastomeric resin compositions so as to render them flame retardant.

BACKGROUND OF THE INVENTION

Many flame retarding agents and methods of application have been developed in attempts to obtain flame resistant textile materials and thermoplastic, thermosetting and elastomeric resin compositions.

Flame retardant textiles have been produced by depositing metal oxides, within or on the textile fibers, by the successive precipitation of ferric oxides and a mixture of tungstic acid and stannic oxide or by successive deposition of antimony trioxide and titanium dioxide. Such processes require plural treatment baths in which strongly acidic solutions are employed thus posing the problem of possible textile degradation. Furthermore, metal oxide coatings on textile materials create difficulties in subsequent dyeing processes which deleteriously affect the hand of the finished product. Another process involves the use of a single processing bath wherein a dispersion of a chlorinated hydrocarbon and finely divided antimony oxide is padded on the textile material. Near the textile combustion temperature antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen orthophosphate. Textile products so treated however are subjected to metathesis reaction with cations during washing, and must be regenerated by reacting the wash product with an ammonium chloride solution.

The production of thermoplastic, thermosetting and elastomeric resin compositons which are flame retardant is of considerable commercial importance. For example, such articles as castings, moldings, foamed or laminated structures and the like are required, or are at least desired, to be resistant to fire and flame and to possess the ability to endure heat without deterioration. The use of various materials incorporated into thermoplastic, thermosetting and elastomeric resins so as to improve the flame retardancy thereof has been known. Many compounds have been commercially available for such use, among them being chlorostyrene copolymers, chlorinated paraffin wax in admixture with triphenyl styrene, chlorinated paraffins and aliphatic antimonical compounds, as well as antimony oxide-chlorinated hydrocarbon mixtures. A problem associated with these compounds has been however, the fact that generally a large amount, i.e., upwards of 35% of additive, must be incorporated into the resin in order to make it sufficiently flame retardant. Such large amounts of additive may deliteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

OBJECTS OF THE INVENTION

It is, therefore, a principal object of this invention to provide novel compounds of the formula:

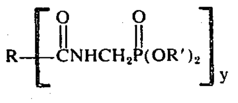

wherein R' is selected from the group consisting of phenyl, lower alkenyl and halogen substituted and unsubstituted lower alkyl of 1–6 carbon atoms, y is an integer from 1–2 provided that when y is 1, R is selected from the group consisting of hydrogen, lower alkyl of 2–8 carbon atoms, benzyl, dialkylphosphonoalkyl and phenoxymethylene and when y is 2, R is lower alkylene of 1–4 carbon atoms.

It is also an object of this invention to provide flame retarding textile materials comprising normally flammable cellulosic, proteinaceous or analogous man-made materials. Another object is to provide a method for treating normally flammable cellulosic, proteinaceous or analogous man-made materials to render them flame retardant. Another object is to provide flame retarding thermoplastic, thermosetting or elastomeric resin compositions comprising normally flammable resin materials. A further object is to provide a process for treating normally flammable thermoplastic, thermosetting or elastomeric resin compositions to render them flame retardant. A particular object is to devise a composition comprising normally flammable cellulosic, proteinaceous or analogous man-made materials and an effective flame retardant amount of the compound represented by the formula

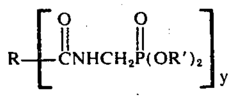

wherein R, R' and y are as above described.

A further particular object is to devise a composition comprising normally flammable thermoplastic, thermosetting or elastomeric polymer and an effective flame retarding amount of the before described novel compound.

These and other objects of the present invention will be obvious from the following description.

DESCRIPTION OF THE INVENTION

In accordance with this invention there are provided novel compounds, for imparting flame retardancy to textiles and resin materials, of the formula

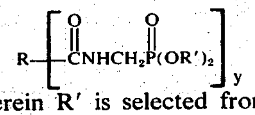

wherein R' is selected from the group consisting of phenyl, lower allyl and halogen substituted and unsubstituted lower alkyl of 1–6 carbon atoms, y is an integer from 1–2 provided that when y is 1, R is selected from the group consisting of hydrogen, lower alkyl of 2–8 carbon atoms, berzyl, dialkylphosphonoalkyl and phenoxymethylene and when y is 2, R is lower alkylene of 1–4 carbon atoms. More specifically, the preferred compounds of the present invention include these compounds wherein R' is lower alkyl of 1–6 carbon atoms.

Illustrative examples of compounds of the present invention include, for instance, compounds of the general formula such as

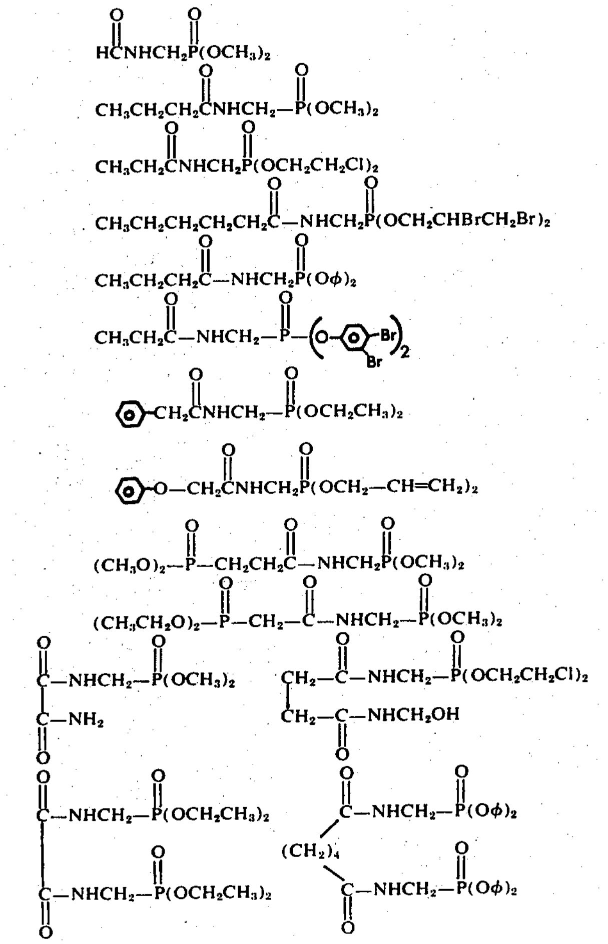

The synthesis of the compositions of the present invention is accomplished by reacting a N-hydroxymethyl amide of the formula

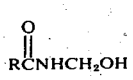

with a trialkyl phosphite of the formula $(R'O)_3P$ wherein R and R' are as previously described in a suitable solvent an excess of phosphite or neat. Typically, the reaction occurs at elevated temperatures and is continued for about 1 to about 12 hours. Temperatures are generally about 50°C to about 160°C. Preferably reaction is continued from about 3 to about 6 hours at a temperature of about 80°C to about 120°C. The solvent or other volatile matter, is thereafter stripped, or otherwise removed from the product. Suitable solvents include benzene, toluene, xylene, glymes, dimethyl formamide, aliphatic or aromatic hydrocarbons. Typical N-hydroxymethyl amides operable as reactants herein include

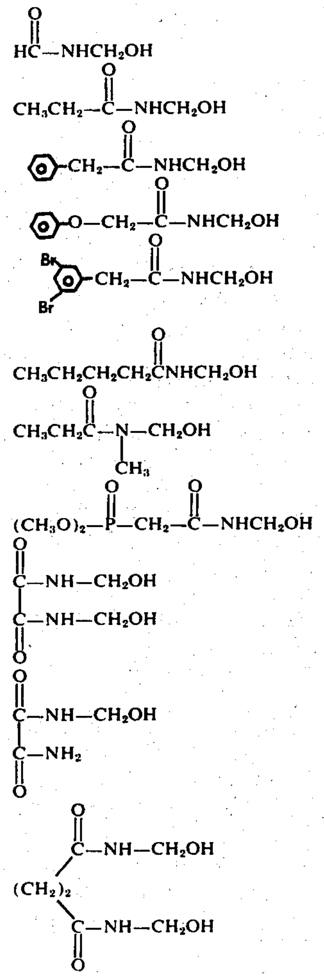

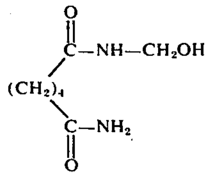

One or more of the novel compounds of this invention may be applied to textile materials by conventional finishing techniques such as by thermal induced pad curing so as to incorporate into the textile a flame retardant amount thereof. The compounds of this invention have advantages over the flame retardant agents of the prior art in that they may be used on a variety of textile materials of different chemical composition, and they may be applied by a variety of methods. They may be applied to materials in either the fiber or fabric form to give flame retarding materials with minimum detectable physical changes in the quality or hand of the textile material.

Products of this invention may be applied to cellulosic materials in several ways to give a durable flame retardant treatment. For example, the products of this invention may be reacted with formaldehyde to give N-hydroxymethyl derivatives which can react with cellulosic materials in a known manner. Alternatively aqueous mixtures of the products with formaldehyde, urea, trimethylol melamine or other known cellulose crosslinking agents may be applied to cellulose substrate with the aid of an acidic catalyst by a padding process.

More preferably the N-hydroxymethyl derivative of the products of this invention prepared by the condensation of the products with formaldehyde, are mixed in an aqueous medium with trimethylol melamine and a Lewis acid catalyst such as $NH_4Cl$ or $Zn(NO_3)_2.6H_2O$. The cellulosic material is immersed in a aqueous solution of the methylol derivative, trimethylol melamine, and $Zn(NO_3)_2.6H_2O$ and squeezed on a two roll padder to 70–90% wet weight pick-up. The material is dried at 220°–270°F for 1–3 minutes and cured at 300°–370°F for 1–6 minutes in a circulating air oven. The samples are then washed in hot water and dried. The finished samples have a flame retardant add-on of about 5 to about 40% and preferably about 10 to about 25% by weight.

The flame retardant agents of this invention may be applied to various textiles such as cellulosic materials, proteinaceous materials and blends of cellulosic or proteinaceous materials with analogous manmade fibers. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs.

The flame retardant compounds or additives of the invention may be incorporated into resin compositions by any known method. That is to say, the flame retardant additive may be added to the resin by milling the resin and the additive on, for example, a two-roll mill, or in a Banbury mixer etc., or it may be added by molding or extruding the additive and resin simultaneously, or by merely blending with the resin in powder form and thereafter forming the desired article. Additionally, the flame-retardant may be added during the resin manufacture, i.e., during the polymerization procedure by which the resin is made, provided the catalysts etc. and other ingredients of the polymerization system are inert thereto. Generally, the compounds of this invention may be incorporated into the thermoplastic resin in flame-retarding amounts, i.e. generally amounts ranging from about 5% by weight, to about 50% by weight, preferably from about 20% weight, to about 40% by weight, based on the weight of the polymer, have been found sufficient.

Resins embraced within the scope of this invention include the homopolymers and copolymers of unsaturated aliphatic, alicyclic, and aromatic hydrocarbons. Suitable monomers are ethylene, propylene, butene, pentene, hexene, heptene, octene, 2-methylpropene-1, 3-methylbutene-1, 4-methylpentene-1, 4-methylhexene-1,5-methylhexene-1, bicyclo-(2.2.1)-2-heptene, butadiene, pentadiene, hexadiene, isoprene, 2,3-dimethylbutadiene-1,3, 2-methylpentadiene-1,3, 4-vinylcyclohexene, vinylcyclohexene, cyclopentadiene, styrene and methylstyrene, and the like.

Other polymers in addition to the above-described olefin polymers that are useful in the invention include polyindene, indenecoumarone resins; polymers of acrylate esters and polymers of methacrylate esters, acrylate and methacrylate resins such as ethyl acrylate, n-butyl methacrylate, isobutyl methacrylate, ethyl methacrylate and methyl methacrylate; alkyd resins and paint vehicles, such as bodied linseed oil; cellulose derivatives such as cellulose acetate, cellulose acetate butyrate, cellulose nitrate, ethyl cellulose, hydroxyethyl cellulose, methyl cellulose and sodium carboxymethyl cellulose; epoxy resins; furan resins (furfuryl alcohol or furfuralketone); hydrocarbon resins from petroleum; isobutylene resins (polyisobutylene); isocyanate resins (polyurethanes); melamine resins such as melamine-formaldehyde and melamine-urea-formaldehyde; oleo-resins; phenolic resins such as phenol-formaldehyde, phenolic-elastomer, phenolic-epoxy, phenolic-polyamide, and phenolic-vinyl acetals; polyamide polymers, such as polyamides, polyamide-epoxy and particularly long chain synthetic polymeric amides containing recurring carbonamide groups as an integral part of the main polymer chain; polyester resins such as unsaturated polyesters of dibasic acids and dihydroxy compounds, and polyester elastomer and resorcinol resins such as resorcinolformaldehyde, resorcinol-furfural, resorcinol-phenol-formaldehyde, resorcinol-polyamide and resorcinol-urea; rubbers such as natural rubber, synthetic polyisoprene, reclaimed rubber, chlorinated rubber, polybutadiene, cyclized rubber, butadiene-acrylonitrile rubber, butadiene-styrene rubber, and butyl rubber; neoprene rubber (polychloroprene); polysulfides (Thiokol); terpene resins; urea resins; vinyl resins such as polymers of vinyl acetal, vinyl acetate or vinyl alcohol-acetate copolymer, vinyl alcohol, vinyl chloride, vinyl butyral, vinyl chloride-acetate copolymer, vinyl pyrrolidone and vinylidene chloride copolymers; polyformaldehyde; polyphenylene oxide; polymers of diallyl phthalates and phthalates; polycarbonates of phosgene or thiophosgene and dihydroxy compounds such as bisphenols, phosgene, thermoplastic polymers of bisphenols and epichlorohydrin (trade named Phenoxy polymers); graft copolymers and polymers of unsaturated hydrocarbons and unsaturated monomer, such as graft copolymers of polybutadiene, styrene and acrylonitrile, commonly called ABS resins; ABS polyvinyl chloride polymers, recently introduced under the trade name of Cycovin; and acrylic polyvinyl chloride polymers, known by the trade name Kydex 100.

The polymers of the invention can be in various physical forms, such as shaped articles, for example, moldings, sheets, rods, and the like; fibers, coatings, films and fabrics, and the like.

The compounds of this invention have been found to have particular utility in ABS resins and in elastomeric materials such as acrylic rubber; acrylonitrile-butadiene styrene terpolymers; butadieneacrylonitrile copolymers; butyl rubber; chlorinated rubbers, e.g., polyvinyl chloride resins, chloroprene rubber, chlorosulfonated polyethylene; ethylene polymers, e.g., ethylene-propylene copolymers, ethylene-propylene terpolymers; fluorinated rubbers, butadiene rubbers, e.g., styrene-butadiene rubber, isobutylene polymers, polybutadiene polymers, polyisobutylene rubbers, polyisoprene rubbers; polysulfide rubbers; silicon rubbers; urethane rubbers; high styrene resins latices, high styrene resins, vinyl resins; sponge rubber; and the like.

It should be noted that it is also within the scope of the present invention to incorporate such ingredients as plasticizers, dyes, pigments, stabilizers, antioxidants, antistatic agents and the like to the novel composition.

ASTM Test D2863-70, used in accordance with the following examples, generally provides for the comparison of relative flammability of self-supporting plastics by measuring the minimum concentration of oxygen in a slowly rising mixture of oxygen and nitrogen that will support combustion. The procedure encompasses supporting cylindrical test specimens 70-150 × 8.0 mm vertically in a glass tube fitted with controlled upward oxygen/nitrogen gas flow. The top of the specimen is ignited and oxygen flow is adjusted until it reaches that minimum rate at which the specimen is extinguished before burning 3 minutes or 50 mm whichever happens first. The oxygen index(n) is then calculated as follows:

$$n,\% = (100 \times O_2)/(O_2+N_2)$$

wherein $O_2$ is the volumetric flow of oxygen, at the minimal rate and $N_2$ is the corresponding volumetric flow rate of nitrogen.

A modification of ASTM Test D635-68 used in accordance with the following examples, generally provides for the comparison of burning rates, self-extinguishment and non-burning characteristics of plastics in the form of sheets, bars, plates or panels. The procedure encompasses preparing cylindrical plastic samples of 150–200 mm × 8 mm diameter with and without the subject flame retardant additive. Each sample is marked at points 1 inch and 4 inches from its end and held, marked end in the flame, at a 45° angle in a controlled burner flame (1 inch flame length) for two 30 second attempts. The movement of the flame up the length of the sample through the two points is measured for rate of burning, non-burning or self-extinguishing characteristics. A sample is rated SE(self-extinguishing) if the flame burns through the first point but extinguishes before reaching the second point. A sample is rated NB(non-burning) if, upon ignition it does not burn to the first point.

AATCC test method 34–1969, The Vertical Char Test, used in accordance with the following examples, generally provides for the comparison of relative flammability of 2¾ inch × 10 inch fabric test specimens when exposed to a controlled burner flame, under controlled conditions, for periods of 12.0 and 3.0 seconds. Charred specimens are thereafter subjected to controlled tearing tests, using tabulated weights, to determine the average tear length as representing the char length of the fabric. In addition, samples which are wholly consumed by the flame are rated (B) and samples which do not burn are rated (NB). For comparison purposes, it should be noted that untreated samples of the fabrics used in the examples of this case would be consumed for this test.

In all the examples of the application, the following general procedure was used except when otherwise specifically noted. Padding was done on a standard two roll laboratory padder at a gauge pressure of about 60 pounds per square inch in all cases. Drying and curing during processing were done with a standard laboratory textile circulating air oven. Washing and drying was done in a standard, home, top loading, automatic washer and dryer. A Hooker Boil (HB) is done in a standard, center post, wringer washer fitted with internal steam coils. The sample to be treated is washed and agitated therein for 45 minutes in a solution containing 88 pounds of water, 100 grams of sodium carbonate, 100 grams of "Ivory" soap and 10 grams of "Tide" detergent at a temperature of about 200° to about 210° Fahrenheit. The washer is then drained, the sample squeezed through the wringer and again washed and agitated therein for 15 minutes in about 88 pounds of water at about 140° to about 160° Fahrenheit.

The following examples are set forth for purposes of illustration only and are not to be construed as limitations of the present invention except as set forth in the appended claims. All parts and percentages are by weight unless otherwise specified.

EXAMPLE I

Preparation of $$H\overset{O}{\overset{\|}{C}}NHCH_2\overset{O}{\overset{\|}{P}}(OCH_3)_2$$

N-hydroxymethyl formamide (0.5 mole) was mixed with trimethyl phosphite (0.5 mole) in a round bottomed, three necked flask fitted with a thermometer, reflux condenser with take off and a magnetic stirrer. The mixture was heated slowly to about 100°C and distillate collected for about 2 hours. The distillate was identified by infrared analysis as methanol. After the distillate ceased the reaction mixture was heated to about 120°C and held at that temperature for about ½ hour. The mixture was then stripped on a rotary evaporator at about 80°C and 5 mm Hg, for about 1 hour to remove all volatiles. The resulting product was identified as N-dimethylphosphonomethyl formamide and was obtained in 98% yield.

EXAMPLE II

Preparation of $$CH_3CH_2CH_2\overset{O}{\overset{\|}{C}}NHCH_2\overset{O}{\overset{\|}{P}}(OCH_3)_2$$

In a 500 ml. round bottomed flask was placed 81.9g (0.70 mole) of N-hydroxymethylbutyrlamide and 124g (1.0 mole) of trimethyl phosphite. The mixture heated to reflux and held at that temperature for about 6 hours. The reaction was then cooled stripped, at 100°C and 2 mm Hg pressure, to remove any volatiles. Infrared and nuclear magnetic resonance spectroscopy identified the product as essentially pure N-dimethylphosphonomethylbutyrlamide in 76.7% yield.

EXAMPLE III

A flask, fitted with reflux condenser, stirrer and thermometer, was charged with 88g (0.5 mole) N,N'-bis hydroxymethyl succinamide and 186g (1.5 mole) trimethyl phosphite and was refluxed at about 92° for about 4 hours. 100 mls. of toluene was added to the reaction and reflux was continued for 25 hours. The reaction mixture was cooled and solidified by addition of 500 mls. acetone. The reaction mixture was then filtered to give 12g solid (mp 236°–245°). Infrared spectra and elemental analysis indicated the solid was succinamide.

The filtrate was then stripped, under 10 mm Hg vacuum at 70°C to give 182g of amber liquid. This liquid was further distilled under vacuum to remove excess trimethyl phosphite. After distillation 144g of amber liquid liquid remained.

The structure was confirmed by elemental analysis and infrared and nuclear magnetic resonance spectroscopy to be N,N'-Bis(dimethylphosphonomethyl) succinamide.

EXAMPLE IV

A 1 liter flask was fitted with reflux condenser, stirrer and thermometer. The flask was charged with 430g. (1.86 mole) of N-hydroxymethyl diethylphosphonoacetamide and 248g (2.0 mole) of trimethyl phosphite. The reaction mixture was heated for about 13 hours at about 105°C. Excess trimethyl phosphite was removed by vacuum distillation to give 528.5g of a thick yellow liquid.

The product structure was confirmed by elemental analysis and infrared and nuclear magnetic resonance spectroscopy to diethylphosphonoacetamide.

EXAMPLE V

Preparation of

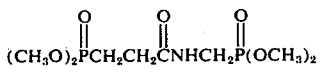

Trimethyl phosphite (2.0 mole) was mixed with N-hydroxymethyl-3-dimethylphosphonopropionamide (1.0 mole) in a one liter flask, fitted with thermometer, mechanical stirrer, distillate take off, and reflux condenser, and heated to reflux for about 2 hours. A mixture of methanol and trimethyl phosphite was removed as distillate and an equivalent volume of trimethyl phosphite added during the second hour of reflux.

After the heating period, when no more methanol was evident in the distillate, the excess phosphite was removed under reduced pressure. The product, a clear viscous oil, was obtained in 95% yield and was the structure N-dimethylphosphonomethyl-3-dimethyl phosphonopropionamide which was confirmed by elemental analysis and infrared spectroscopy.

EXAMPLE VI

Preparation of

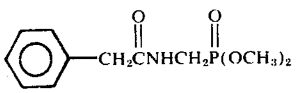

A 500 ml. round bottomed flask was charged with 124g (1.0 mole) of trimethyl phosphite and heated to 100°C. To this was added 132g (0.8 mole) of N-hydroxymethylphenylacetamide over a ten minute period of time. The mixture was held at about 96° for about 6 hours, cooled, filtered, and stripped, at 100°C. and 0.25 mm Hg, to give a 64% yield of the desired product in the form of a pale yellow oil. Elemental analysis as well as infrared and nuclear magnetic resonance spectroscopy confirmed the structure.

EXAMPLE VII

Preparation of

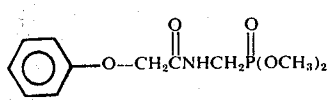

Trimethyl phosphite (62g 0.5 mole) was heated to about 100°C in a round bottomed flask. N-hydroxymethylphenoxyacetamide (54g, 0.3 mole) was added over a 5.0 minute time period and the mixture heated at about 92° for about 2 hours. After the heating period the mixture was stripped, at 100°C and 0.5 mm pressure, to give a 90% of the desired product.

EXAMPLE VIII

Preparation of

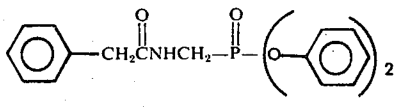

N-hydroxymethyl phenyl acetamide (14.0g 0.085 mole) was heated with triphenyl phosphite (27g 0.085 mole) at 120°–124°C for about 5 hours in a round bottomed flask. The reaction mixture was then stripped, at 120°C and 2 mm pressure, to remove phenol and other volatile material to give the desired product (29.4g). The product was confirmed by infrared and nuclear magnetic resonance spectroscopy.

EXAMPLE IX

Preparation of

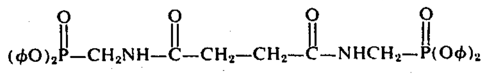

In a 250 ml round bottomed flask 17.6g of N,N'-bis hydroxymethyl succinamide and 62g of triphenyl phosphite were heated at about 130°C for about 5 hours. Upon completion of the heating the reaction mixture was stripped, at 120°C and 2 mm Hg, to remove phenol and other volatile material. The product was a thick yellow semi solid and was obtained in 89.3% yield. The structure of the desired product was confirmed by spectroscopic and elemental analyses.

EXAMPLE X

Preparation of

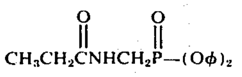

N-diphenyl phosphonomethyl propionamide, was prepared in 82.2% yield by heating N-hydroxymethylpropionamide (0.2 mole) and triphenyl phosphite (0.2 mole) at about 130° for about 5 hours. After the heating period was complete phenol was removed under reduced pressure (2 mm Hg) at 120°. The product structure was confirmed by infrared and nuclear magnetic resonance spectroscopy.

EXAMPLE XI

Preparation of

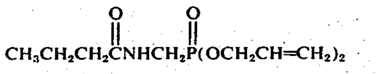

Triallyl phosphite (40.2g 0.2 mole) was mixed with N-hydroxymethyl butyramide 23.4g 0.2 mole) in a round bottomed flask and heated about 4 hours at about 125°C. At the end of this time the reaction mixture was stripped at about 125°C and 2 mm pressure. The product obtained was a red-brown liquid and its structure was confirmed by elemental analysis and infrared and nuclear magnetic resonance spectroscopy.

EXAMPLE XII

Preparation of

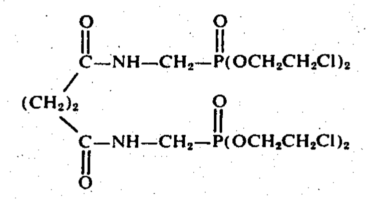

A mixture of tris-2-chloroethyl phosphite (0.2 mole) and N,N'-bis-hydroxymethyl succinamide (0.1 mole) was heated in a round bottomed flask at about 130°C for about 6 hours. The reaction mixture was then stripped, at 100°C and 2 mm Hg pressure, to remove any volatile material. 43 grams of N,N'-bis-(2-chloroethyl)phosphonomethyl succinamide was obtained as a brown wax.

EXAMPLE XIII

Thirty parts of N-dimethylphosphonomethyl butylamide and seventy parts of polystyrene were dry blended for about 5 minutes. This mixture was then brought to a melt and mixed thoroughly for about 15 minutes, cooled, and chopped into small pieces. These pieces were then molded into a solid cylinder 200 mm × 8 mm and tested by ASTM tests D2863-70 and D635-68 as described below. Results of these tests are contained in Table I.

EXAMPLES XIV-XXVI

Using the procedure of Example 13, various plastic compositions were prepared and tested containing various flame retardants. The results are set forth in Table I.

EXAMPLE XXVII 5.0 oz. cotton sheeting was padded through a solution containing 30 parts of N-dimethylphosphonomethyl-3-dimethylphosphonopropionamide, 10 parts of trimethylolmelamine, 30 parts of 40% formalin solution, 25 parts of water and 5 parts of $Zn(NO_3)_2.6H_2O$.

The sheeting was squeezed to a 80% wet pick-up by means of a two roll laboratory padder, and thereafter dried at about 250°F for about 2 minutes and cured at about 340° for about 4 minutes in a circulating air oven. The sheeting was then washed for one wash cycle, in a standard home type automatic washer with Tide detergent and tumble dried. A resin add-on of 24.7% was obtained. The sheeting was then subjected to AATCC test method 34–1969 and had a calculated char length of 4.5 inches. The sheeting was then subjected to one hooker boil and when tested by AATCC test method 34–1969 had a calculated char length of 5.5 inches.

EXAMPLE XXVIII 8.0 oz. per sq. yd. wool Bedford cord was padded through the solution of Example XXVII and squeezed to 60% wet pick-up. After drying curing and washing as in Example XXVII a Resin add-on of 17.7% was obtained. Initial testing under AATCC test method 34–1969 indicates a 1.5 inch calculated char length. The wool Bedford cord was then subjected to 24 additional washes in a standard home type automatic washer using Tide detergent and tumble dried. Testing by method 34–1969 indicated a calculated char length of 3.0 inches.

EXAMPLE XXIX

A rayon staple fiber sample was immersed in the solution of Example XXVII and squeezed to 100% weight gain. The sample was dried for 5 minutes at 240°F and cured 10 minutes at 340°F, washed in hot tap water, and dried to give a 32% add-on.

A treated sample is self-extinguishing if ignited in a bunsen flame and then removed while an untreated sample is completely consumed.

The treated sample remains self-extinguishing after 10 home washes in an automatic washer.

EXAMPLE XXX

A solution of N-dimethylphosphonomethylphenyl acetamide (0.2 mole) and 38% formalin solution (0.2 mole) in 50 g of water was refluxed about 1 hour at a pH of 9 and then stirred an additional 3 hours at room temperature. The pH was adjusted to 7.0 and 20g of trimethylolmelamine and 5g of magnesium chloride hexahydrate added. 5.0 oz. cotton sheeting was padded through the solution and squeezed to a wet pick-up of 120% on a two roll laboratory padder. The sheeting was then dried at about 240°F for about 2 minutes and cured at about 350°F for about 3 minutes in a circulating air oven. The sheeting was then washed by hand for about 5 minutes using Tide detergent. Testing under AATCC method 24–1969 gave a 2.0 inch calculated char length. After subjected to a second hand washing as above described, testing gave a 1.9 inch calculated char length.

EXAMPLE XXXI

N,N'-bis-dimethylphosphonomethyl succinamide (40g) was mixed with 40% formalin solution (60g) and stirred overnight at a pH of 10. The pH was then adjusted to 7.0 with hydrochloric acid and 23g of a 50% solution of a methylolated malamine and 5g of ammonium chloride added.

6.0 oz. sq. yd. wool sample was padded through the solution and squeezed to about 130% wet pick-up on a two roll laboratory padder at 60 lb. gauge pressure. The treated wool was then dried at about 250°F for about 2 minutes and cured at about 350°F for about 4 minutes in a circulating air oven. The treated wool was then washed by hand for about five minutes using Tide detergent and tumble dried. A resin add-on of 41% and oxygen index of 28 was calculated. The thus treated wool was then subjected to AATCC method 34–1969 and found to have a calculated char length of 3.0 inches. The treated wool was then subjected to 4 additional hand washes, on above described, and after testing by method 34–1969 had a char length of 4.0 inches.

EXAMPLE XXXII

A padding solution was prepared as in Example XXXI using N-dimethylphosphonomethylbutyramide as the phosphorus containing species.

6 oz. per sq. yd. wool was treated by the process of Example XXXI using the above described padding solution. Resin add-on was calculated to be 30% and oxygen index 28. Testing under method 34–1969 after one wash gave a calculated char length of 3.6 inches and after 4 additional washings, a calculated char length of 4.0 inches.

EXAMPLE XXXIII

N-dimethylphosphonomethylforamide (40g) was mixed with 40% formalin solution (60g) and stirred overnight at pH 9–10. The pH was adjusted to 7.0 with hydrochloric acid and then 23g of a 50% solution of a methylolated melamine and 5g of ammonium chloride were added.

A rayon staple fiber was immersed in the above solution and squeezed to about 115% wet pick-up on a two roll laboratory padder. The fiber was then dried in a circulating air oven for about 5 minutes at about 250° and cured about ten minutes at about 350°, washed in hot water by hand, and air dried giving about 32% resin add-on.

The oxygen index of the fiber was calculated as 29.5 as compared to 19.5 for untreated fiber. The treated samples self-extinguished when a Bunsen flame was applied for 2 seconds and removed while untreated samples burned completely. The self-extinguishing character is maintained after 5 hot water, hand washings.

TABLE I

| Example | Polymer | Compound | % Compound in Mixture | OI | D-635 |
|---|---|---|---|---|---|
| XIII | Polystyrene | 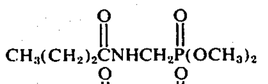 | 30 | — | SE |
| XIV | Polypropylene | 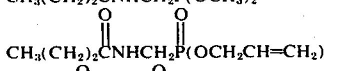 | 40 | — | SE |
| XV | Epoxy | 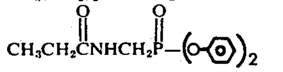 | 35 | 25 | SE |
| XVI | Polyethylene Terephthalate | 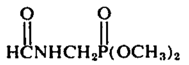 | 30 | 25.5 | NB |
| XVII | Epoxy | 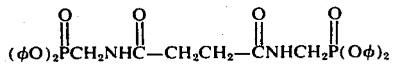 | 40 | 23.5 | — |
| XVIII | Nylon | 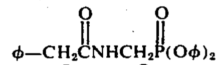 | 30 | 24.9 | NB |
| XIX | Polystyrene | 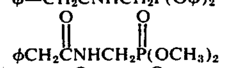 | 40 | 19.4 | — |
| XX | Polystyrene | 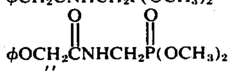 | 40 | 20.5 | — |
| XXI | ABS | '' | 40 | 20 | — |
| XXII | ABS | 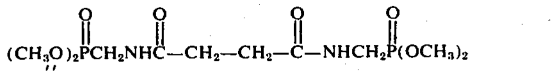 | 40 | 24.6 | — |
| XXIII | Nylon | '' | 40 | 25.0 | — |
| XXIV | Polyethylene Terephthalate | '' | 40 | 34 | NB |
| XXV | SBR | '' | 30 | 20.2 | SE |
| XXVI | Polypropylene | 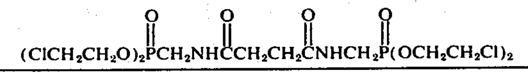 | 30 | 23.5 | SE |

We claim:

1. An article comprising a resin compound and a flame retardant amount of a compound of the formula

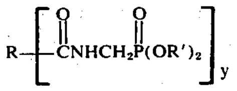

wherein R' is selected from the group consisting of phenyl, lower alkenyl and halogen substituted and unsubstituted lower alkyl of 1–6 carbon atoms, y is an integer from 1–2 provided that when y is 1, R is selected from the group consisting of hydrogen, lower alkyl of 2–8 carbon atoms, benzyl, lower dialkylphosphonoalkyl and phenoxymethylene and when y is 2, R is lower alkylene of 1–4 carbon atoms.

2. The article of claim 1 wherein said compound is

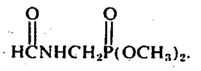

3. The article of claim 1 wherein said compound is

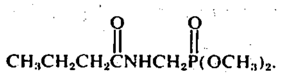

4. The article of claim 1 wherein said compound is

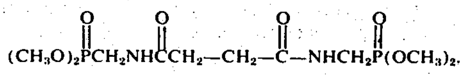

5. The article of claim 1 wherein said compound is

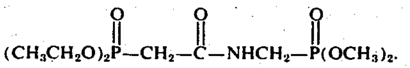

6. The article of claim 1 wherein said compound is

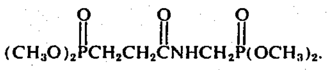

7. The article of claim 1 wherein said compound is

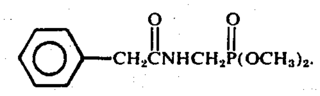

8. The article of claim 1 wherein said compound is

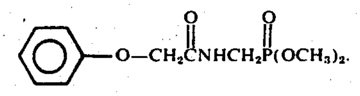

9. The article of claim 1 wherein said compound is

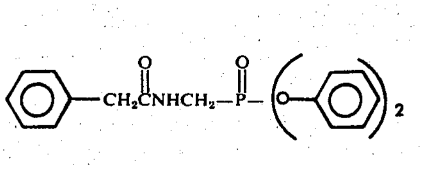

10. The article of claim 1 wherein said compound is

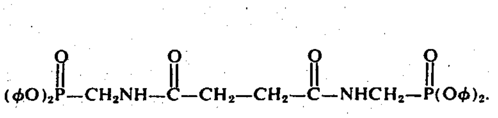

11. The article of claim 1 wherein said compound is

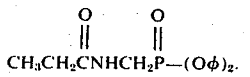

12. The article of claim 1 wherein said compound is

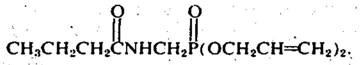

13. The article of claim 1 wherein said compound is

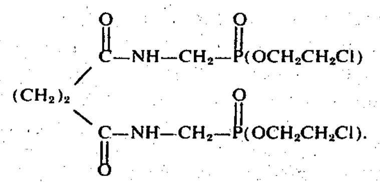

14. A process for rendering thermoplastic resin compositions flame retardant which comprises applying to said resin a flame retardant amount of a compound of the formula

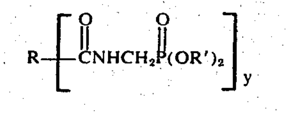

15. A process for rendering thermosetting resin compositions flame retardant which comprises applying to said resin a flame retardant amount of a compound of the formula

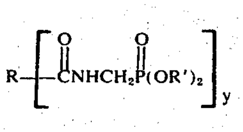

wherein R' is selected from the group consisting of phenyl, lower alkenyl and halogen substituted and unsubstituted lower alkyl of 1–6 carbon atoms, y is an integer from 1–2 provided that when y is 1, R is selected from the group consisting of hydrogen, lower alkyl of 2–8 carbon atoms, benzyl, lower dialkylphosphonoalkyl and phenoxymethylene and when y is 2, R is lower alkylene of 1–4 carbon atoms.

16. A process for rendering elastomeric resin compositions flame retardant which comprises applying to said resin a flame retardant amount of a compound of the formula

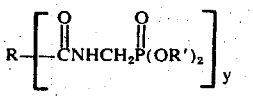

wherein R' is selected from the group consisting of phenyl, lower alkenyl, and halogen substituted and unsubstituted lower alkyl of 1–6 carbon atoms, y is an integer from 1–2 provided that when y is 1, R is selected from the group consisting of hydrogen, lower alkyl of 2–8 carbon atoms, benzyl, lower dialkylphosphonoalkyl and phenoxymethylene and when y is 2, R is lower alkylene of 1–4 carbon atoms.

* * * * *

UNITED STATES PATENT OFFICE

CERTIFICATE OF CORRECTION

PATENT NO. : 3,976,620

DATED : August 24, 1976

INVENTOR(S) : Peter Golborn and James J. Duffy

It is certified that error appears in the above-identified patent and that said Letters Patent are hereby corrected as shown below:

Column 3, line 24, "berzyl" should read -- benzyl --.

Column 6, line 8, "20% weight" should read -- 20% by weight --.

Column 16, line 29, insert ---wherein R' is selected from the group consisting of phenyl, lower alkenyl and halogen substituted and unsubstituted lower alkyl of 1-6 carbon atoms, y is an integer from 1-2 provided that when y is 1, R is selected from the group consisting of hydrogen, lower alkyl of 2-8 carbon atoms, benzyl, lower dialkylphosphonoalkyl and phenoxymethylene and when y is 2, R is lower alkylene of 1-4 carbon atoms.

Signed and Sealed this

Eighth Day of March 1977

[SEAL]

*Attest:*

RUTH C. MASON
*Attesting Officer*

C. MARSHALL DANN
*Commissioner of Patents and Trademarks*